United States Patent [19]
Gupta et al.

[11] Patent Number: 5,728,156
[45] Date of Patent: Mar. 17, 1998

[54] PRISMATIC INTRAOCULAR LENSES AND RELATED METHODS OF IN SITU ALTERATION OF THEIR OPTICAL CHARACTERISTICS

[75] Inventors: Amitava Gupta, Bethesda, Md.; Ronald D. Blum, Roanoke, Va.

[73] Assignee: Prism Opthalmics, L.L.C., Roanoke, Va.

[21] Appl. No.: 693,340

[22] Filed: Aug. 6, 1996

[51] Int. Cl.$^6$ ................................................. A61F 2/16
[52] U.S. Cl. ........................................ 623/6; 351/160 R
[58] Field of Search ................. 623/5, 6; 351/160 R, 351/161

[56] References Cited

U.S. PATENT DOCUMENTS

| | | | |
|---|---|---|---|
| 3,245,745 | 4/1966 | Hancock | 351/167 |
| 4,575,373 | 3/1986 | Johnson | 623/6 |
| 4,581,031 | 4/1986 | Koziol et al. | 623/6 |
| 4,648,878 | 3/1987 | Kelman | 623/6 |
| 4,666,446 | 5/1987 | Koziol et al. | 623/6 |
| 4,685,921 | 8/1987 | Peyman | 623/6 |
| 4,685,922 | 8/1987 | Peyman | 623/6 |
| 4,731,078 | 3/1988 | Stoy et al. | 623/6 |
| 4,779,972 | 10/1988 | Gottlieb | 351/177 |
| 4,787,903 | 11/1988 | Grendahl | 623/6 |
| 4,828,558 | 5/1989 | Kelman | 623/6 |
| 5,002,383 | 3/1991 | Sisler | 351/175 |
| 5,089,023 | 2/1992 | Swanson | 623/6 |
| 5,141,301 | 8/1992 | Morstad | 351/161 |
| 5,151,723 | 9/1992 | Tajiri | 351/161 |
| 5,288,293 | 2/1994 | O'Donnell, Jr. | 623/6 |
| 5,443,507 | 8/1995 | Jacobi | 623/6 |
| 5,549,668 | 8/1996 | O'Donnell, Jr. | 623/6 |

*Primary Examiner*—Mary Beth Jones
*Attorney, Agent, or Firm*—Finnegan, Henderson, Farabow, Garrett & Dunner, L.L.P.

[57] ABSTRACT

Prismatic intraocular lenses are disclosed for restoring visual function to an eye having macular degeneration. The lenses each include a convex lens optic for receiving and focusing light rays, a prismatic wedge located posterior to the convex lens optic for receiving and directing light rays to a first portion of a retina of the eye, and means for in situ alteration of the optical characteristics of the intraocular lens to direct light rays to a second functional portion of the retina.

27 Claims, 5 Drawing Sheets

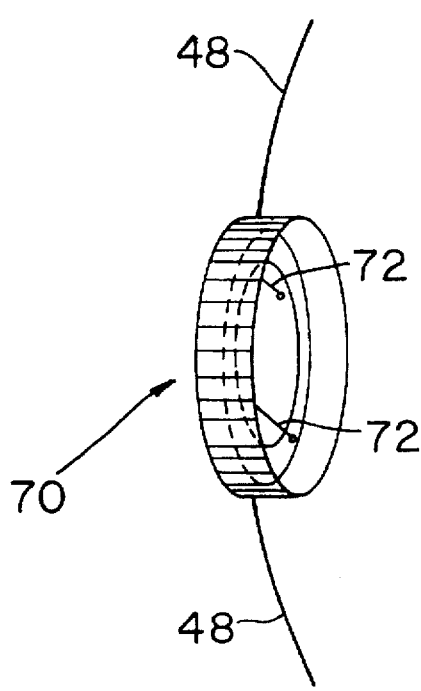
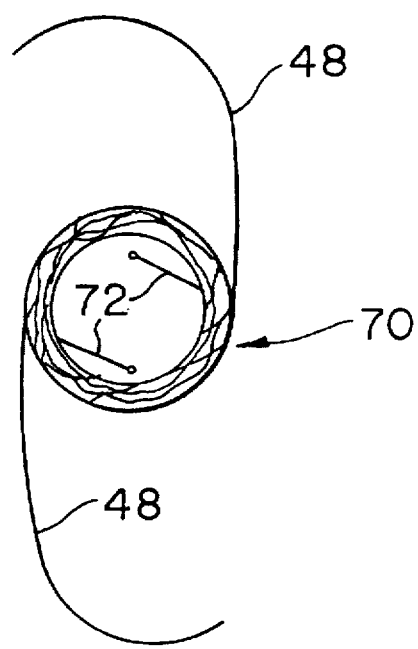
FIG. 7A
FIG. 7B
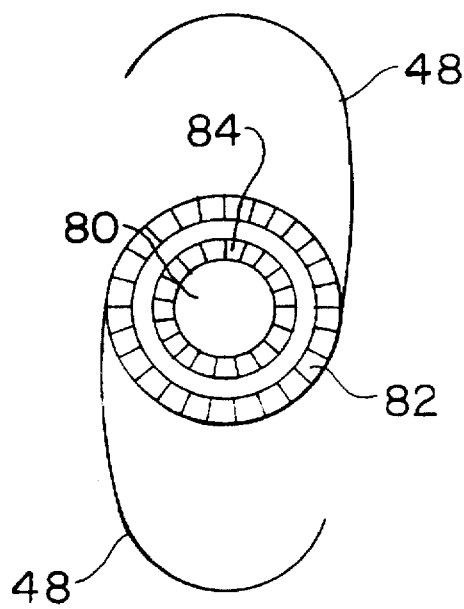
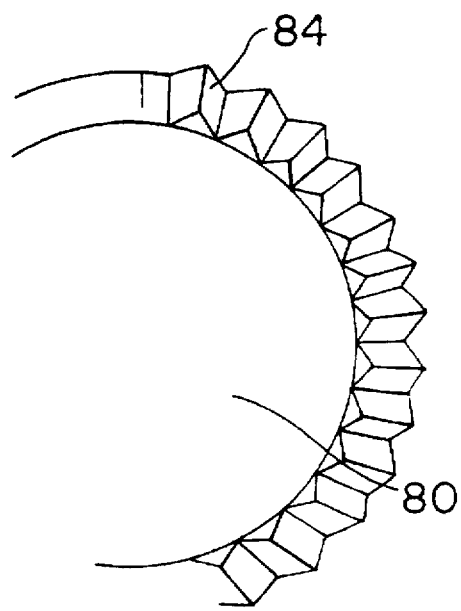
FIG. 8
FIG. 9

PRISMATIC INTRAOCULAR LENSES AND RELATED METHODS OF IN SITU ALTERATION OF THEIR OPTICAL CHARACTERISTICS

BACKGROUND OF THE INVENTION

CROSS-REFERENCE TO RELATED APPLICATION

This application is related to U.S. patent application Ser. No. 08/647,228 filed on May 9, 1996, the content of which is incorporated by reference.

1. Field of the Invention

The present invention relates to prismatic intraocular lenses and related methods of using such lenses to restore vision in patients with macular degeneration. More particularly, the present invention relates to prismatic intraocular lenses and related methods of in situ alteration of their optical characteristics.

2. Description of the Related Art

As shown in FIG. 1, a normal eye 10 includes a cornea 12, an aqueous solution called the aqueous humor 14 behind cornea 12, an iris 16, a natural lens 18, ciliary sulcus 20, retina 22, macula 24 at the center of the retina, and fovea 26 at the center of macula 24. The cornea 12 and lens 18 cause an image 30 to form at fovea 26. Fovea 26 is a circular zone approximately 0.2–0.5 $mm^2$ in area. The image 30 formed at fovea 26 corresponds to a locus of fixation for providing acute vision. This locus of fixation helps to coordinate voluntary and involuntary head and eye movements required for daily activities, such as reading, driving, and dressing. Peripheral images are located around this locus of fixation.

A common cause of blindness in adults is macular degeneration. This retinal disease involves damage to the fovea so that the fovea is unable to process images. The damage spreads over time into the macula and beyond, causing a blind spot at the center of a patient's visual field. The patient is thus unable to read, drive, or perform other tasks that require the brain to reference the locus of fixation.

In most patients, even in those with advanced macular degeneration, the macula is not completely damaged, but retains healthy areas. However, the loss of the locus of fixation caused by the central blind zone leads to severe visual impairment and often to legal blindness, defined as visual acuity of 20/200 or less. The number of patients diagnosed with such severe visual impairment in the United States alone exceeds 2 million.

Intraocular lens implants have been devised to replace the natural lens of the eye and restore sight to damaged or diseased eyes. For example, compound intraocular lenses that combine different optical elements have been proposed. In such proposals, a diffractive/refractive lens implant includes a diffractive lens profile covering about half the effective lens area. Such a configuration allows about half of the incident light from distant objects and half of the incident light from near objects to enter the eye. Such a compound optic provides an ability to form on the retina a focused image of both distant objects and near objects.

Although both images are formed on the fovea, the brightness of the image in each case is reduced by about 50%, or the ratio of the light intensity assigned to each image. In certain cases, such a lens can be used to treat macular degeneration by providing sufficient image magnification so as to project the image over a retinal area more than that damaged by macular degeneration. Such an approach, however, does not shift the image to healthy portions of the retina.

Similar multifocal intraocular lenses incorporating two refractive zones also have been disclosed. For example, the use of a pair of bifocal intraocular lenses has been disclosed in which each of the pair of bifocal intraocular lenses incorporates a refractive element and a diffractive element. One of the lenses provides greater image intensity for the image of near objects, while the other lens provides greater image intensity for the image of distant objects. This approach has the advantage that the incident light can be apportioned or split between the two images in a continuous manner between the two lenses. The disadvantage is that the image is processed by two optical elements, each of which introduces its own aberrations and loss of image contrast so that the performance of the compound lens can be worse than either a diffractive or refractive lens.

Intraocular lenses incorporating a single refractive element also have been devised to shift the image from a damaged portion of the retina to a healthy area. In this respect, a prismatic intraocular lens that includes a convex lens portion for focusing light rays and a prism posterior to the convex lens for deflecting light away from the diseased center of the retina to a functional portion. The prismatic intraocular lens restores the central field vision to a patient.

Several considerations arise before such a prismatic intraocular lens can be prescribed for a patient with central field loss. For example, means to fixate the intraocular lens in the eye has to be developed in order to ensure that the lens does not rotate or tilt. Such displacements would cause the shifted retinal image to move, perhaps back to a zone which has become nonfunctional due to macular degeneration.

Addition of the prism wedge to the intraocular lens optic also causes an increase in the thickness of the optic. Due to the geometry of the eye, it is necessary to minimize the thickness of the prism wedge while remaining thick enough to redirect an image to a desired location on the retina. A methodology to prescribe particular prismatic intraocular lenses for patients also remains to be developed.

Once a patient is implanted with a prismatic intraocular lens, the locus of fixation provided by the prismatic correction remains fixed. Typically, macular disease progresses and may eventually reach the locus of fixation. In such an event, a second surgery typically is performed in order to relocate the locus of fixation to a healthy area of the macula. To reposition or replace the prismatic intraocular lens, this surgical procedure involves incision of eye tissue and insertion of instruments into the eyes and, like other eye surgeries, carries significant health risks.

SUMMARY OF THE INVENTION

Accordingly, an object of this invention is to provide means to alter in situ the optical characteristics of prismatic intraocular lenses necessitated by a progression of a patient's macular disease. Such in situ alterations do not involve incision of eye tissue or insertion of instruments into the eye.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

To achieve the objects and in accordance with the purpose of the invention, as embodied and broadly described herein, the invention comprises an intraocular lens for restoring visual function to an eye having macular degeneration. The lens includes a convex lens optic for receiving and focusing light rays and a prismatic wedge located posterior to the convex lens optic for receiving and directing light rays to a first portion of a retina of the eye. The lens further includes means for in situ alteration of the optical characteristics of the intraocular lens to direct light rays to a second functional portion of the retina.

According to another aspect, the invention comprises an intraocular lens including a convex lens optic for implantation into an eye to receive and focus light rays and a prismatic wedge located posterior to the convex lens optic for receiving and directing light rays to a first focal point on a retina of the eye. The intraocular lens also includes means for altering the direction of the light rays from the first focal point to a second functional focal point on the retina without incision into the eye.

According to a further aspect, the invention comprises a method of redirecting light rays focused on a first portion of the retina by a prismatic intraocular lens having a convex lens optic and a prismatic wedge to a second functional portion of the retina. The method includes the steps of providing the convex lens optic within the eye for receiving and focusing light rays, providing the prismatic wedge within the eye posterior to the convex lens optic for receiving and directing light rays to the first portion, and in situ altering in situ the optical characteristics of the intraocular lens to direct light rays to the second functional portion.

According to an even further aspect, the invention comprises a method for altering a first refractive index profile of a prismatic wedge portion of a prismatic intraocular lens implanted in an eye. The method includes the steps of determining a location of the prismatic intraocular lens within the eye, determining a magnitude of a prism wedge angle, an orientation, and the first refractive index profile of the prismatic wedge portion, computing a second refractive index profile required to shift a locus of fixation from a first portion of a retina of the eye to a second functional portion of the retina, and delivering a controlled set of laser pulses to points on the prismatic wedge portion in order to alter the first refractive index profile to the second refractive index profile and shift the locus of fixation from the first portion of the retina to the second functional portion of the retina.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate an embodiment of the invention and together with the description, serve to explain the principles of the invention. In the drawings.

FIG. 7A is a side perspective view of a cylindrical member and haptics in which a prismatic intraocular lens is mounted for use according to the present invention;

FIG. 7B is a plan view of the cylindrical member and haptics of FIG. 7A;

FIG. 8 is a plan view of a prismatic intraocular lens and an outer mounting ring according to a further embodiment of the present invention; and FIG. 9 is an enlarged partial plan view of the prismatic intraocular lens shown in the FIG. 8 embodiment.

DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts.

The present invention is directed to prismatic intraocular lenses and related methods of in situ alteration of their optical characteristics. Prismatic intraocular lenses and four related methods of altering their optical characteristics are disclosed. Although these methods are suitable for use in connection with any single prismatic intraocular lens, the methods will be described in connection with the use of a pair of intraocular lenses for restoring visual function to patients with central field loss. A description of this pair of lenses and their characteristics follows. It will be understood that the lenses and related methods of the invention, to be described later, are not limited to their use in connection with this pair of lenses.

To restore vision in patients with central field loss, a first intraocular lens is provided in a first eye to provide vision of distant targets, those which are more than five feet away from the eye. A second intraocular lens is provided in the second eye of the patient to provide vision of targets within close range, about twelve inches or less from the eye, and preferably, within about three to nine inches from the eye.

Each intraocular lens includes a single refractive means to deflect the position of the image from a blind spot at the center of the eye, possibly a macular hole, to a functional area in the retina. Preferably, the single refractive means comprises a prismatic wedge integrally connected to a convex lens portion. Use of a single refractive means improves the total modulation transfer function delivered by the optic, in other words, improves the contrast versus resolution performance of the optic.

As discussed below, the prism wedge angle necessary for shifting a retinal image for particular patients must be accurately determined. The thickness of the prismatic intraocular lens is controlled by fabricating the lens from certain materials having specific indices of refraction, also as detailed below.

Figure 1:
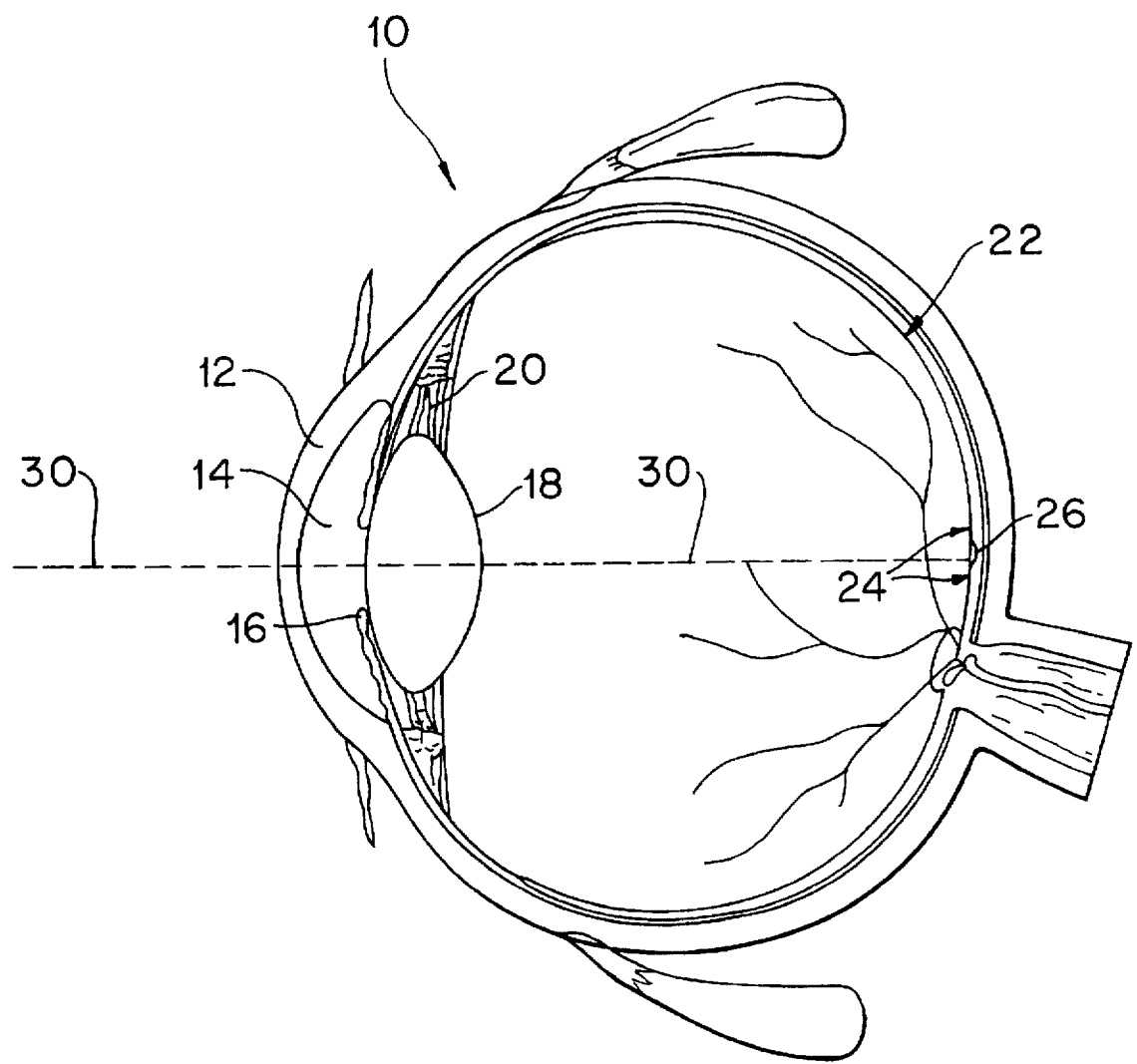
FIG. 1 is a side elevation sectional view of a normal human eye having a natural lens.
Figure 2:
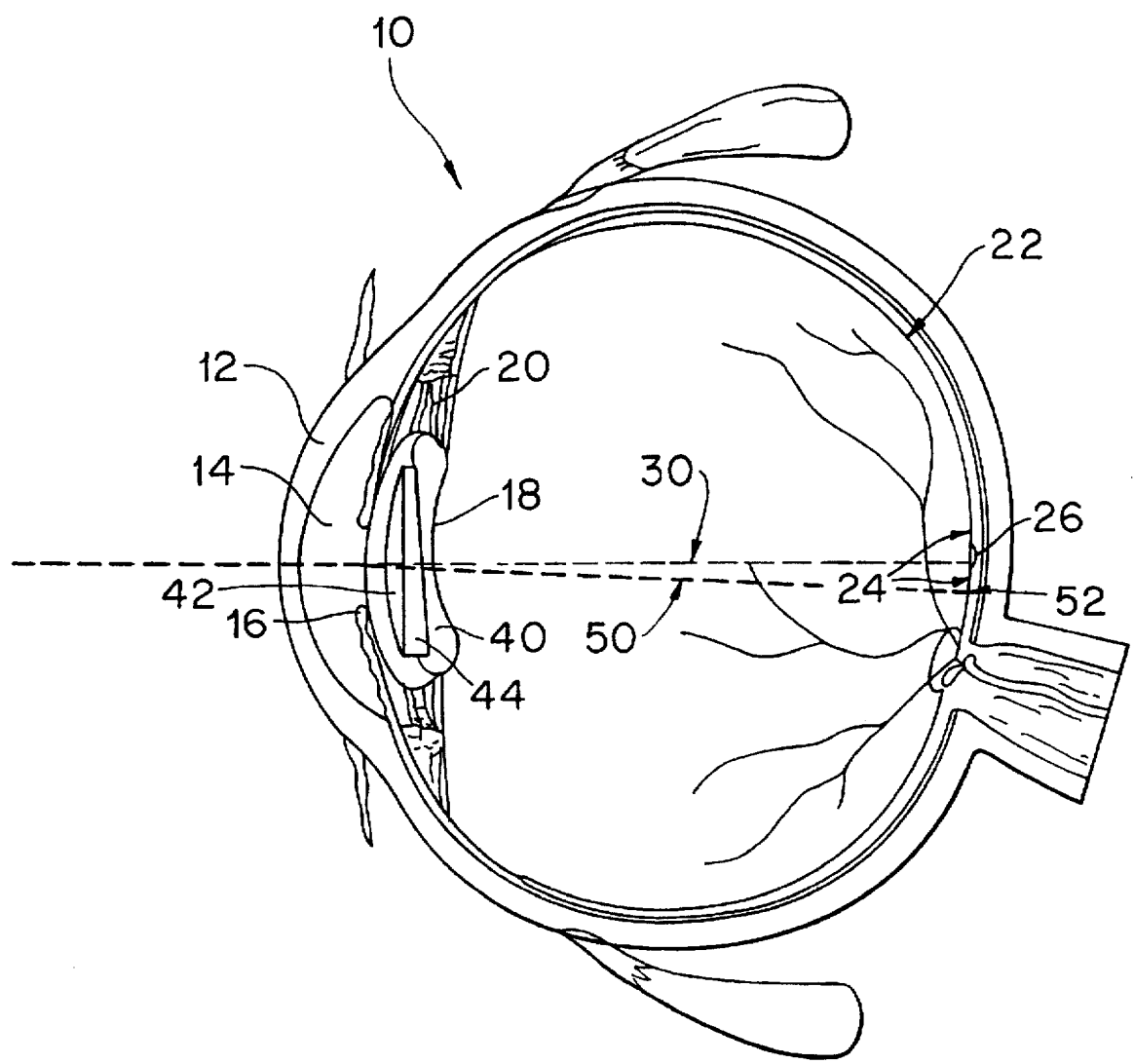
FIG. 2 is a side elevation sectional view of an eye incorporating a prismatic intraocular lens according to the present invention.
Figure 3:
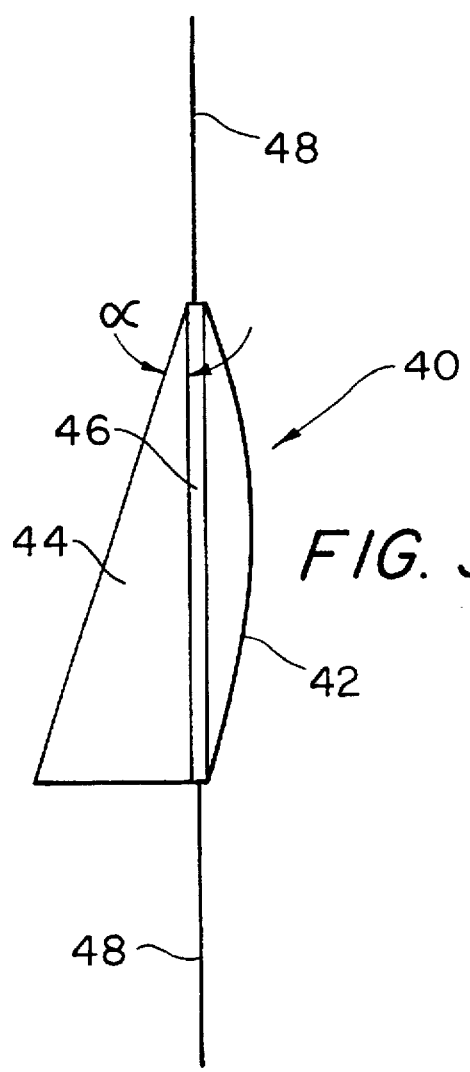
FIG. 3 is a side elevation view of the prismatic intraocular lens and haptics shown in FIG. 2.

As shown in FIGS. 2 and 3, a prismatic intraocular lens 40 includes a convex lens portion 42 for focusing the image and a prism wedge 44 posterior to the lens portion for redirecting the image to a functional portion of the retina. As shown in FIG. 2, image 30 that forms at fovea 26 in a normal eye will be redirected to image 50 for shifting the image location to a healthy retinal area 52. A base portion 46 of the intraocular lens 40 defines the width and thickness of the haptics 48 that are described further herein.

Figure 5:
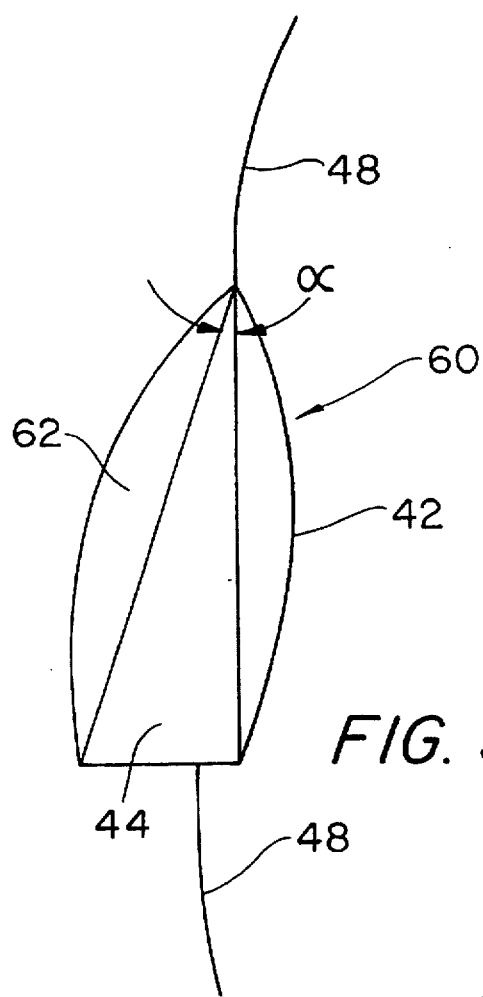
FIG. 5 is a side elevation view of another embodiment of a prismatic intraocular lens according to the present invention.

FIG. 5 shows another embodiment of a prismatic intraocular lens, denoted by reference numeral 60. In this embodiment, the convex lens portion 42 is directly connected to the prism wedge 44. Haptics 48 extend from opposing portions of prism wedge 44. A portion 62 forms the posterior convex refracting portion and allows smooth contact of the lens with the posterior capsule.

A precise determination of the magnitude of angle α of prism wedge 44 is necessary to accurately shift the image to healthy retinal areas. In order to accurately determine prism wedge angle α, a patient with visual impairment due to central field loss in both eyes is subjected to a series of diagnostic tests to determine the position of healthy, functional areas of the retina. Precise measurements are made to determine the distance from the fovea to the desired points of image fixation in each eye. Once functional areas are located, one eye is selected for vision of distant targets while the other is used for near vision.

The magnitude of angle α of prism wedge 44 for both lenses is then calculated according to the following equation:

$$\alpha = 360 d / 2\pi (n_1 - n_2)$$

where

α=magnitude of prism wedge angle in degrees;

d=the distance from the fovea to the desired healthy point of image fixation on the retina;

$n_1$=the refractive index of the prismatic intraocular lens material;

$n_2$=the refractive index of the aqueous solution in the aqueous humor, typically about 1.334; and a=the distance from the fovea to the posterior plane of the intraocular lens.

The distances d and a are determined form the patient's diagnostic tests. The refractive index $n_1$ of the prismatic intraocular lens is determined as described further below.

As a second step to sufficiently specify the intraocular lens optic for each eye, it is necessary to couple the magnitude of the prism wedge angle with the spherical power of each prismatic intraocular lens. The spherical power is the reciprocal of the focal length of the lens, and may be specified for best corrected distance vision or near vision. The spherical power of the intraocular lens depends on the length of the optic axis of the eye and the spherical power of the cornea. The optic axis of the eye is determined by ultrasonic imaging of the eye, a standard procedure preceding the removal of the crystalline lens of the eye and implantation of an intraocular lens. Corneal power is determined by measuring corneal curvature and corneal thickness, again through standard ultrasonic image scanning techniques.

As mentioned, the thickness of the prismatic intraocular lens for use in the methods of the present invention must be controlled. For the preferred placement in the capsular sac, the maximum thickness of the lens is approximately 3.8 mm. Lenses thicker than 3.8 mm can be implanted into the ciliary sulcus. Implantation of the lens in the ciliary sulcus, anterior to the anterior lens capsule, can occur after performing a posterior capsulotomy followed by a vitrectomy. In such a case, or in the case of the implantation of the lens into the capsular fornix, the thickness of the lens should be controlled so as to not contact and thereby traumatize the iris.

Two methods may be used to minimize the thickness of the intraocular lens. First, aspheric optics reduce the intraocular lens thickness and also improve the quality of the retinal image by minimizing spherical aberration. In aspheric optics, the geometry of the lens surface (either anterior or posterior) is adjusted to correct for spherical aberration and to restore image contrast at the focal point. The corrected surface is aspheric in shape.

In a second method of reducing the thickness of the lens, the thickness of the prism wedge can be reduced by fabricating the prism wedge and convex lens portion from a material of high refractive index. The prism wedge angle required for a particular image shift decreases as the refractive index increases. The thickness of the prism wedge necessary for a particular image shift, therefore, decreases as the refractive index of the prism increases.

For various refractive indices, Table 1 shows the corresponding prism angles (α) needed for a retinal shift d=1.0 mm when a=17 mm (the lens is positioned 17 mm from the fovea). The last column of Table 1 shows the increase in lens thickness that the prismatic wedge adds to a 6.0 mm diameter intraocular lens.

TABLE 1

| REFRACTIVE INDEX $n_1$ OF THE OPTIC MATERIAL | PRISM WEGDE ANGLE REQUIRED FOR 1.0 mm SHIFT, α(DEGREES) | ADDED THICKNESS TO A 6.0 mm DIAMETER INTRAOCULAR LENS (mm) |
|---|---|---|
| 1.50 | 20 | 2.2 |
| 1.56 | 14.7 | 1.6 |
| 1.60 | 12.5 | 1.3 |

As shown, by using a material of refractive index 1.6 as compared to one of refractive index 1.5, the overall thickness of the prismatic intraocular lens decreases by 0.9 mm.

A preferred material for 1–2 mm image shifts is polymethyl methacrylate (PMMA) having a refractive index of 1.498. For shifts greater than 2.0 mm, a material of higher refractive index should be used. An image shift of 3.0 mm or greater is rarely encountered since visual acuity drops steeply radially away from the fovea to as much as 20/200 or lower.

A material of refractive index in the range of 1.5–1.6 can be achieved through the polymerization of a suitable mixture of mono and/or multifunctional monomers and oligomers and a polymerization initiator. The polymerization can occur through an addition polymerization or a condensation polymerization process. Monomers and oligomers susceptible to addition polymerization include acrylates, methacrylates, styrenics, or allytic derivatives. Preferred examples of acrylate and methacrylate monomers for an addition polymerization reaction include phenyl ethyl acrylate, phenoxy ethyl acrylate, trifluoromethyl acrylate, ethyl acrylate, methyl methacrylate, and acrylic terminated organic phosphites and phosphine oxides. Preferred examples of acrylate and methacrylate oligomers for an addition polymerization reaction include polyethylene glycol diacrylate, polyethylene glycol dimethacrylate, aliphatic alkoxy diacrylate ester (code SR 9209 from Sartomer Corp.), bisphenol A diacrylate, and bisphenol A dimethacrylate. Epoxides, anhydrides, and silane derivative are among the preferred materials for condensation polymerization.

Combinations of these polymerizable derivatives produce biocompatible polymerizable formulations that form optically clear polymers with a refractive index in the range 1.5–1.6. The preferred selection of monomers and oligomers depends on biocompatibility as measured by standard toxicological tests, tissue compatibility, and lastly, when essential, implantation of intraocular lenses into the eyes of live animals.

The polymerization reactions of the preferred mixture may be carried out by the application of heat, light, or both. To fabricate the intraocular lens, the mixture may be either poured directly into molds shaped to form the lens, or formed into optical quality rods or sheets. The rods or sheets are then cored by a machining process to form buttons used in lens manufacture.

Each prismatic intraocular lens, according to the present invention, must be firmly supported and fixed within the eye to lessen its susceptibility to rotational displacement. Unwanted rotational displacement will potentially move the deflected image from a healthy retinal area to a dysfunctional area.

Figure 4:
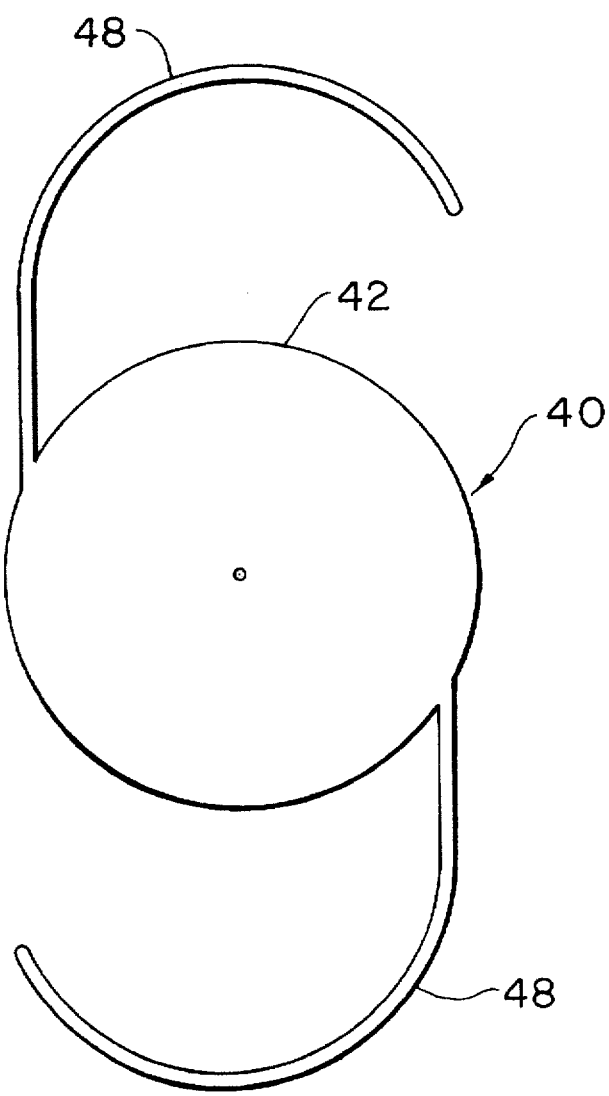
FIG. 4 is a front elevation view of the prismatic intraocular lens and haptics of FIG. 3.

In the preferred embodiment, haptics 48, shown in FIGS. 3 and 4, are used to support and fix intraocular lens 40. The compressive force exerted by haptics 48 on the convex lens optic 42 prevents its rotational or tilting displacement and ensures its stability.

Preferably, each haptic 48 is integrally formed with the prismatic intraocular lens 10 to form a single piece construction. Each haptic 48 radiates out from the intraocular lens 10 in the form of a modified C. Haptics 48 may be formed from the same polymerizable materials described above for the lenses.

Because prismatic intraocular lenses 10, according to the present invention, can weigh two to three times more than conventional intraocular lenses, and therefore require extra stability, haptics 48 must not be overly flexible. The trend in conventional haptic design is to decrease the compressive restoring force to as low as 80 mg of restoring force per millimeter of compression. According to the present invention, it has been found that a compressive restoring force for each haptic 48 is preferably in the range of 150–250 mg of restoring force per millimeter of compression, when measured with reference to overall relaxed dimensions. This higher restoring force increases the stability of the prismatic intraocular lens.

The axis joining the haptic-optic junction points is preferably located orthogonally to the prism axis. Such a configuration permits haptics of equal cross-section and easier polishing of the haptic-optic junction.

As mentioned, the disclosed prismatic intraocular lenses shift retinal images to a functional portion of the retina. Should that portion become nonfunctional due to a progression of macular degeneration, it is necessary to further shift the retinal images to a second functional portion of the retina.

The present invention includes prismatic intraocular lenses and four related embodiments of methods for in situ alteration of the optical properties of prismatic intraocular lenses. In the first method, the refractive index profile of the intraocular lens, particularly the prismatic wedge portion, is altered by laser pulses. By altering the refractive index, angular and/or linear displacements of the locus of fixation can result. In a second method of in situ alteration, a prismatic contact lens modifies the location of the focus of the prismatic intraocular lens. According to a third embodiment of the invention, laser pulses mechanically displace the prismatic intraocular lens to alter the locus of fixation. In a fourth embodiment, laser pulses directed at angulated edges of the lens optic portion of the prismatic intraocular lens angularly or linearly displace the intraocular lens to alter the locus of fixation. A description of each of these embodiments follows.

According to a first embodiment of the present invention, the refractive index profile of the prism wedge portion of a prismatic intraocular lens is altered upon irradiation by laser pulses. The alteration in the refractive index will displace the locus of fixation either linearly (radially outward) or angularly. According to this embodiment, the intraocular lens must be constructed from a material which undergoes an alteration of its refractive index upon irradiation with a laser pulse. The laser pulse has a wavelength which is transmitted by the cornea and the anterior humor, absorbed by the lens of the eye, and does not harm the retina or other eye tissue.

To achieve a linear (radially outward) displacement of the locus of fixation without causing a change in the angular location of the focus with respect to the fovea, a uniform alteration of the refractive index of the prismatic portion is required. With reference to Table 1, a prism wedge of a material with a refractive index of 1.50 and a 20° angle results in a 1.0 mm retinal shift. To increase the magnitude of the shift from 1.0 mm to 1.25 mm, a refractive index increase of 0.043 units is required. This is calculated by using the equation given above. Thus, if the refractive index of the prism wedge portion of a prismatic intraocular lens increases from 1.50 to 1.543 upon irradiation with laser pulses, then the locus of alternate fixation will move linearly outward by 0.25 mm.

A significant benefit of this approach is that a patient implanted with an intraocular lens capable of undergoing a refractive index change may be treated on an outpatient basis, similar to a procedure used currently for laser assisted posterior capsulotomy. In that procedure, a pulsed neodymium yttrium aluminum garnet (Nd:YAG) laser lasing at 1.06 microns is used to incise the posterior capsule if it develops a haze and thus reduces vision.

The angular orientation of the locus of fixation, as opposed to the linear (radial) orientation, may also be displaced by means of altering the refractive index of the prism wedge portion of the prismatic intraocular lens. To change the angular orientation, the profile of the refractive index within the prism wedge is nonuniformly altered, instead of a uniform alteration in the refractive index. For example, a radial shift of 0.089 mm, measured along the circumference of a circle whose radius is the line joining the fovea to the point of the original shift, is needed to shift the locus of fixation by 5 degrees from its original position for a 1.0 mm displacement from the fovea. Such a radial shift can be achieved by altering the refractive index of the prismatic portion by 0.014 units. To achieve this, the location of the lens within the eye is imaged and recorded by means of a camera or a biomicroscope. The location of the lens is input into a software program which controls the steering mechanism for the laser beam. The program accepts as input parameters the required angular shift and the location of the prismatic intraocular lens and its optical characteristics, including the spherocylindrical power of the lens, the magnitude and orientation of the prism, and the refractive index of the lens material. The program computes the refractive index profile required to cause the desired angular shift of the locus of fixation and the number of laser pulses to be delivered at each point of the lens surface in order to achieve this altered refractive index profile. The pulsed laser system will thus be used to deliver a controlled set of pulses at various points on the lens surface following a protocol computed by the control software.

Combined angular and linear displacements of the locus of fixation may be achieved in one protocol of laser induced alteration of the refractive index profile of the prismatic wedge portion of the intraocular lens. The spherical power of the intraocular lens may also be changed if the lens portion of the optic incorporates material which undergoes a refractive index change upon exposure to laser pulses, and if the laser pulse is focused on the lens portion. Specific parts of the lens optic may be altered in this manner to, for example, form a bifocal or multifocal lens. The relationship between the degree of alteration of the refractive index achieved and the change in spherical power of the lens is expressed as follows:

$$\Delta D = \Delta n \left( \frac{1}{R_1} - \frac{1}{R_2} \right)$$

where $\Delta D$=change in spherical power of the lens;

$\Delta n$=change in refractive index;

$R_1$ is one of the radii of curvature of the lens; and $R_2$ is the other radius of curvature of the lens.

Thus, the power of a 20 diopter (20D) lens can be increased by 1.0D by increasing the refractive index of a material with base index of 1.50 by 0.0075 units.

As mentioned, laser pulses used to effect a refractive index change must be of a wavelength which is not absorbed by the cornea or the aqueous humor. A wavelength range from about 0.320 microns to about 1.10 microns is appropriate. A preferred example of a laser pulse is to use a near UV laser pulse with a pulse width in the order of 1–50 nanoseconds. This laser pulse is generated by frequency doubling a dye laser output. The prismatic intraocular lens optic material is designed to completely absorb the laser pulse, protecting the retina from the laser energy. The laser pulse may be focused on specific points on the optic surface effecting a pattern of change of the refractive index, similar to that described above.

In a second preferred example of suitable laser pulses, picosecond pulses with energy densities in the gigawatt range are used. Each such pulse carries 1010 to 1012 photons. The pulse repeat frequency is left quite low, i.e., the duty cycle is maintained at 5% or lower. The advantage of delivering energy in this manner is to be able to reduce the total amount of energy delivered to the eye and to achieve better control of the energy delivered to the lens optic.

The interaction of the laser pulse with the lens optic material may involve multiphoton processes, in which simultaneous (or sequential) absorption of two or more laser photons is required to elevate the material to the desired electronically excited state, which causes a change in molecular configuration needed for the change in refractive index. In that case, the efficiency of utilization of the input laser energy to effect changes in refractive index is higher at higher peak laser powers. Picosecond laser pulse trains with high peak powers and low duty cycles specified in order to limit the input of total energy into the eye is required for this process of laser interaction. Utilization of long wavelength laser pulses intrinsically less harmful to the retina is made possible by multiphoton mechanisms. It is to be understood that the present invention places no limit on the type of interaction required between the laser pulse and the material. The foregoing is provided only as nonlimiting examples of interactions between laser photons and plastic materials leading to changes in refractive index of the latter. Other suitable interactions known in the art may be employed to effect refractive index changes in prismatic lens material.

Materials which have the potential to change their refractive index upon irradiation with laser pulses are known and have been used in optical computing and information storage. Such materials may incorporate groups such as carbon-carbon double bonds which undergo isomerization reactions, dimers of aromatic nuclei which may form or open interfacial dimers, or other structures which undergo ring opening or ring closing reactions from their electronically excited states. Examples are cis and trans cinnamic acids, dimers of phenazine, anthracene and its derivatives, etc. These materials may also contain photocrosslinkable groups. Certain hydrophilic materials may be made to increase their cross link density upon exposure to laser pulses which in turn reduces the level of hydration. One example of a photocrosslinkable group is a thiocarbonyl (C=S) moiety. These groups dimerize upon photoexcitation to form a crosslink involving a —C—S—S—C— linkage. Other groups which undergo photodimerization may also be utilized for this purpose. The most preferred example of a material is a hydrophilic polymer incorporating olefinic linkages which undergo laser induced photocyclization and hence enhance the crosslink density.

Materials incorporating photoreactive groups similar to those described above may be formed by copolymerization or grafting reactions. The intraocular implant may be fabricated by machining a blank of such a material. Alternatively, the implant may be made by case molding an appropriate formulation of monomers and initiators including monomers with photoactive substituents. Yet another method of fabrication of such an implant may involve blending two or more polymers or copolymers together with a crosslinking agent, at least one of which bears a photoactive group as defined above, then vulcanizing the mixture to form a transparent blend in the form of a sheet, rod, or the lens body itself. If the material is formed in the form of a sheet or rod, the lens is fabricated by means of a series of machining and polishing steps.

According to a second embodiment of the present invention, a prismatic contact lens is used to modify the location of the focus of the prismatic intraocular lens which remains undisturbed in the eye. In such an arrangement, a contact lens is positioned so that its prismatic shift is parallel to the prismatic shift provided by the intraocular lens. A contact lens with a prism of 1.5D (diopter), for example, will shift the locus of fixation radially outward by 0.25 mm.

Figure 6:
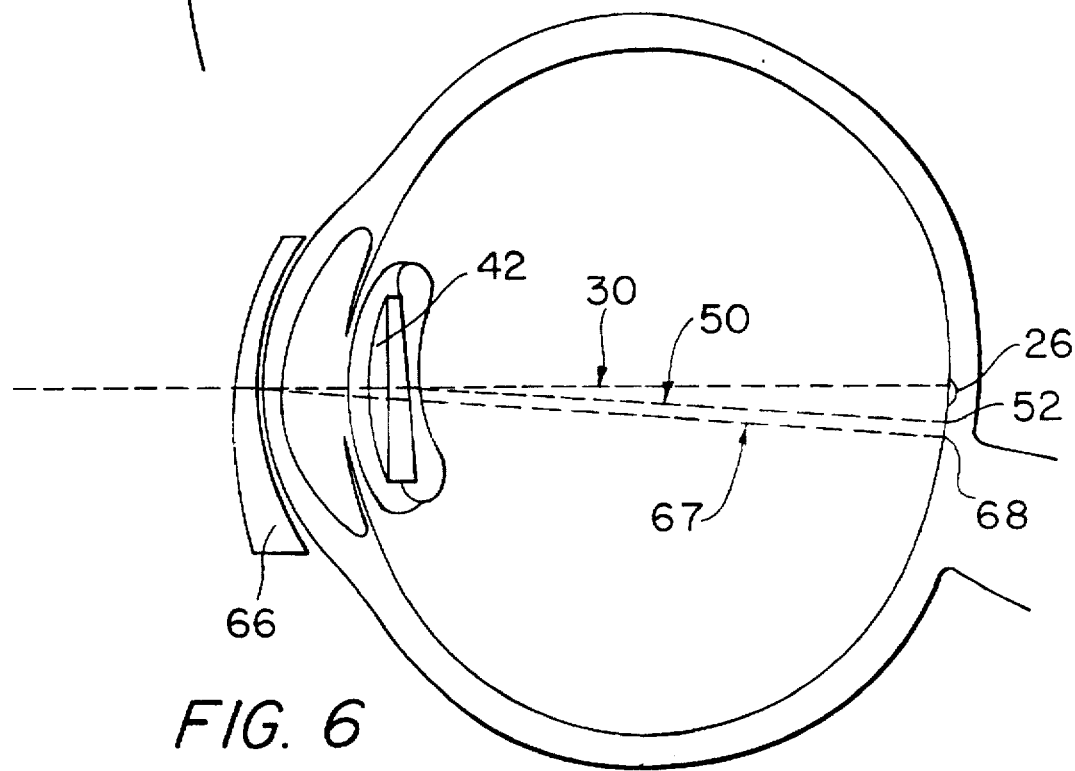
FIG. 6 is a side elevation sectional view of an eye incorporating a prismatic intraocular lens and a prismatic contact lens according to the present invention.

FIG. 6 is a schematic diagram of a prismatic contact lens, denoted by reference numeral 66, used in combination with a prismatic intraocular lens 42. FIG. 6 shows the image path 30 formed at fovea 26 in the absence of both the prismatic contact lens 66 and the intraocular lens 42, and the image path 50 shifted to an originally healthy retinal area 52 when using only the prismatic intraocular lens. When using both contact lens 66 and intraocular lens 42, prismatic contact lens 66 shifts the original image prior to intraocular lens 42 receiving the image. Intraocular lens 42 then shifts the image along path 67 to a healthy area 68 of the retina.

A contact lens suitable for this arrangement is made with no additional spherocylindrical power correction, i.e., it is a plano lens. The contact is weighted so that the prism wedge remains fixed at a desired angular orientation. To clear the lens and correctly position it on the eye, a patient may require assistance from a health care provider.

According to a third embodiment of the invention, the lens optic portion of a prismatic intraocular lens is mechanically displaced by laser pulses or other suitable sources of energy which may be used, once again, without making an incision into the eye. According to this embodiment, the prismatic intraocular lens optic is mounted inside an outer cylindrical member which is attached to the haptics. The outer cylindrical member is fixed within the eye after implantation.

FIGS. 7A and 7B show an embodiment of an outer cylindrical member, denoted generally by reference numeral 70. The prismatic intraocular lens mounts inside cylindrical member 70 and remains free to rotate inside cylindrical member 70. The intraocular lens may be attached to member 70 by means of one or more attachments 72 which can expand or contract when exposed to energy, such as heat or laser energy. Alternatively, one or more attachments 72 may be cut or incised by the incident energy. The intraocular lens rotates as the length of one or more attachments 72 is altered by incident energy. The most preferred example of a material for the attachments 72 is a shrinkable plastic material such as polypropylene fabricated in the form of a suture, which shrinks on application of thermal energy. Other suitable materials known in the art, for example polyethylene or polyvinylacetate, may be used for attachments 72. Cylindrical member 70 may be made of polymethyl methacrylate or other similar suitable materials.

Specific portions of attachments 72 can be shrunk at a time, causing rotational or linear displacement of the intraocular lens optic. Attachments 72 are arranged so that the prismatic intraocular lens optic remains stable under normal environmental conditions of temperature and humidity. To displace the intraocular lens optic, or the prismatic portion thereof, one or more attachments 72 are modified by means of energy pulses, e.g., laser pulses, ultrasonic energy pulses, or other suitable energy pulses. The intraocular lens may be rotated about or displaced along the optic axis by this method. Displacing the lens along the optic axis alters its spherical correction, while a rotation in a plane perpendicular to the optic axis shifts the focus radially along an arc with the fovea being at the center without changing the magnitude of the shift.

If a laser is used to provide the energy needed to alter the tension of attachments 72, the laser should be of a wavelength such that it is readily transmitted by the cornea and the aqueous humor, i.e., of wavelength between about 0.320 microns and about 1.10 microns. A particularly appropriate laser for such an application is a pulsed laser with a high energy density (joules per unit area per pulse) and low power density (a low duty cycle, i.e., a relatively small number of short pulses per second). Such a pulsed laser delivers the maximum motive force to attachments 72, while depositing the minimum quantity of total energy that must be dissipated within the eye by surrounding ocular tissue.

According to a fourth embodiment of the present invention, the prismatic intraocular lens optic is displaced angularly (rotation) or linearly by directing a laser pulse at the edge of the optic which is provided with structure for propelling the optic. As shown in FIGS. 8 and 9, a prismatic intraocular lens 80, including a lens portion and a prismatic wedge portion, is mounted within an outer ring 82. The outer ring 82 is preferably made of plastic, most preferably polymethyl methacrylate, or silicone rubber. Lens 80 is frictionally coupled to ring 82 so as to permit forced rotation of lens 80 within ring 82 which remains fixed and stationary. This relationship is achieved by having the diameter of lens 80 equal to or larger than the inner diameter of the outer ring 82. More specifically, if the inner diameter of lens 80 is a+/−b mm, then the inner diameter of ring 82 is (a−2b)+/−b mm. These tolerances ensure that the diameter of lens 80 is equal to or greater than the inner diameter of ring 82. The tolerances further ensure a tight fit between lens 80 and ring 82, preventing free rotation of lens 80 within ring 82.

Lens 80 may be displaced by applying a mechanical force to lens 80. As shown most clearly in FIG. 9, intraocular lens 80 according to one embodiment includes raised and angulated structures 84 positioned at the periphery of lens 80. Structures 84 are preferably comprised of plastic. When a laser pulse of appropriate power is focused on structures 84, the energy of the laser pulse is converted into thermal and mechanical energy forcing rotation of lens 80 within outer ring 82. Outer ring 82 forms a seal with the posterior capsule and thus prevents incursion of residual lens epithelial and cortical cells along the capsular surface towards the edge of the optic, minimizes synechae, and allows the lens optic to rotate relative to outer ring 82.

The above-described prismatic intraocular lenses and related methods of in situ alteration of the optical characteristics of prismatic intraocular lenses alter the locus of fixation, and compared to conventional eye surgeries, have significantly less health risks. It will be understood, however, that a patient with central field loss needs time to adapt to the altered locus of fixation. A patient needs from 1–2 minutes to 1–2 months to allow adaption of his/her oculomotor skills to the newly established locus of fixation and thereby derive full benefit from the altered locus of fixation.

It will be apparent to those skilled in the art that various modifications and variations can be made in the inventive prismatic intraocular lenses and related methods of in situ alteration of the optical characteristics of prismatic intraocular lenses without departing from the scope or spirit of the invention. It is intended that the specification and examples be considered as exemplary only, with a true scope and spirit of the invention being indicated by the following claims.

What is claimed:

1. An intraocular lens for restoring visual function to an eye having macular degeneration, the lens comprising:
    a convex lens optic for receiving and focusing light rays;
    a prismatic wedge located posterior to the convex lens optic for receiving and directing light rays to a first portion of a retina of the eye; and
    means for in situ alteration of the optical characteristics of the prismatic wedge to direct light rays to a second functional portion of the retina.

2. The intraocular lens according to claim 1, wherein the altering means comprises a material having a refractive index capable of changing upon the incidence of laser radiation, the prismatic wedge being comprised of the material.

3. The intraocular lens according to claim 2, wherein a profile of the refractive index of the material of the prismatic wedge undergoes a uniform change upon the incidence of laser radiation.

4. The intraocular lens according to claim 2, wherein a profile of the refractive index of the material of the prismatic wedge undergoes of a nonuniform change upon the incidence of laser radiation.

5. An intraocular lens for restoring visual function to an eye having macular degeneration, the lens comprising:
    a convex lens optic for receiving and focusing light rays;
    a prismatic wedge located posterior to the convex lens optic for receiving and directing light rays to a first portion of a retina of the eye; and
    means for in situ alteration of the optical characteristics of the intraocular lens to direct light rays to a second functional portion of the retina, wherein the altering means comprises a material having a refractive index capable of changing upon the incidence of laser radiation, the prismatic wedge being comprised of the material.

6. The intraocular lens according to claim 5, wherein a profile of the refractive index of the material of the prismatic wedge undergoes a uniform change upon the incidence of laser radiation.

7. The intraocular lens according to claim 5, wherein a profile of the refractive index of the material of the prismatic wedge undergoes a nonuniform change upon the incidence of laser radiation.

8. The intraocular lens according to claim 5, wherein the material is a hydrophilic polymer incorporating olefinic linkages.

9. A lens system for restoring visual function to an eye having macular degeneration, the system comprising:

an intraocular lens having a convex lens optic for receiving and focusing light rays and a prismatic wedge located posterior to the convex lens optic for receiving and directing light rays to a first portion of a retina of the eye; and means for directing light rays to a second functional portion of the retina comprising a prismatic contact lens positioned over the eye for altering a location that the convex lens optic receives light rays.

10. A lens system for restoring visual function to an eye having macular degeneration, the system comprising:

an intraocular lens having a convex lens optic for receiving and focusing light rays and a prismatic wedge located posterior to the convex lens optic for receiving and directing light rays to a first portion of a retina of the eye; and means for in situ alteration of the optical characteristics of the intraocular lens to direct light rays to a second functional portion of the retina, wherein the altering means comprises a member implanted within the eye for mounting the convex lens optic and the prismatic wedge, the member including means for attaching the convex lens optic and the prismatic wedge to the member, the attaching means comprised of a material that changes size upon exposure to incident energy.

11. The intraocular lens according to claim 10, wherein the material is a shrinkable plastic material.

12. An intraocular lens for restoring visual function to an eye having macular degeneration, the lens comprising:

a convex lens optic for receiving and focusing light rays;

a prismatic wedge located posterior to the convex lens optic for receiving and directing light rays to a first portion of a retina of the eye; and means for in situ alteration of the optical characteristics of the intraocular lens to direct light rays to a second functional portion of the retina, wherein the altering means comprises raised members connected to a surface of the convex lens optic for displacing the intraocular lens upon the incidence of laser radiation.

13. An intraocular lens for restoring visual function to an eye having macular degeneration, the lens comprising:

a convex lens optic for receiving and focusing light rays;

a prismatic wedge located posterior to the convex lens optic for receiving and directing light rays to a first portion of a retina of the eye; and means for in situ alteration of the optical characteristics of the intraocular lens to direct light rays to a second functional portion of the retina, wherein the altering means comprises a ring arranged at the periphery of the convex lens optic, the ring including raised structures for displacing the intraocular lens upon the incidence of laser radiation.

14. The intraocular lens according to claim 12 or 13, further comprising means for mounting and permitting forced rotation of the convex lens optic and the prismatic wedge within the eye.

15. The intraocular lens according to claim 13, further comprising a fixed outer ring and frictional members for mounting and permitting forced rotation of the convex lens optic and the prismatic wedge within the eye.

16. A method of redirecting light rays focused on a first portion of the retina by a prismatic intraocular lens having a convex lens optic and a prismatic wedge to a second functional portion of the retina, the method comprising the steps of:

providing the convex lens optic within the eye for receiving and focusing light rays;

providing the prismatic wedge within the eye posterior to the convex lens optic for receiving and directing light rays to the first portion;

in situ altering the optical characteristics of the prismatic wedge to direct light rays to the second functional portion.

17. The method according to claim 16, wherein the altering step includes altering a refractive index profile of a material comprising the prismatic wedge.

18. The method according to claim 17, wherein the refractive index profile is uniformly altered by laser radiation.

19. The method according to claim 17, wherein the refractive index profile is nonuniformly altered by laser radiation.

20. A method of redirecting light rays focused on a first portion of the retina by a prismatic intraocular lens having a convex lens optic and a prismatic wedge to a second functional portion of the retina, the method comprising the steps of:

providing the convex lens optic within the eye for receiving and focusing light rays;

providing the prismatic wedge within the eye posterior to the convex lens optic for receiving and directing light rays to the first portion;

in situ altering the optical characteristics of the intraocular lens to direct light rays to the second functional portion, wherein the altering step includes altering a refractive index profile of a material comprising the prismatic wedge.

21. The method according to claim 20, wherein the refractive index profile is uniformly altered by laser radiation.

22. The method according to claim 20, wherein the refractive index profile is nonuniformly altered by laser radiation.

23. A method of redirecting light rays focused on a first portion of the retina to a second functional portion of the retina, the method comprising the steps of:

providing a prismatic intraocular lens within the eye, the prismatic intraocular lens having a convex lens optic for receiving and focusing light rays and a prismatic wedge posterior to the convex lens optic for receiving and directing light rays to the first portion; and in situ altering the optical characteristics of the intraocular lens to direct light rays to the second functional portion by providing and positioning a prismatic contact lens over the eye to alter a location that the convex lens optic receives light rays.

24. A method of redirecting light rays focused on a first portion of the retina by a prismatic intraocular lens having a convex lens optic and a prismatic wedge to a second functional portion of the retina, the method comprising the steps of:

providing the convex lens optic within the eye for receiving and focusing light rays;

providing the prismatic wedge within the eye posterior to the convex lens optic for receiving and directing light rays to the first portion;

providing a member within the eye for mounting the convex lens optic and the prismatic wedge, the member having means for attaching the convex lens optic and the prismatic wedge to the member;

in situ altering the optical characteristics of the intraocular lens to direct light rays to the second functional portion, wherein the altering step includes changing a size of the attachment means by exposure to incident energy.

25. A method of redirecting light rays focused on a first portion of the retina by a prismatic intraocular lens having a convex lens optic and a prismatic wedge to a second functional portion of the retina, the method comprising the steps of:

providing the convex lens optic within the eye for receiving and focusing light rays;

providing the prismatic wedge within the eye posterior to the convex lens optic for receiving and directing light rays to the first portion;

in situ altering the optical characteristics of the intraocular lens to direct light rays to the second functional portion, wherein the altering step includes displacing the intraocular lens upon laser radiation incident at raised portions of the convex lens optic.

26. The method according to claim 25, further comprising the step of providing a means for mounting and permitting forced rotation of the convex lens optic and the prismatic wedge within the eye.

27. A method for altering a first refractive index profile of a prismatic wedge portion of a prismatic intraocular lens implanted in an eye, the method comprising the steps of:

determining a location of the prismatic intraocular lens within the eye;

determining a magnitude of a prism wedge angle, an orientation, and the first refractive index profile of the prismatic wedge portion;

computing a second refractive index profile required to shift a locus of fixation from a first portion of a retina of the eye to a second functional portion of the retina; and delivering a controlled set of laser pulses to points on the prismatic wedge portion in order to alter the first refractive index profile to the second refractive index profile and shift the locus of fixation from the first portion of the retina to the second functional portion of the retina.

* * * * *

UNITED STATES PATENT AND TRADEMARK OFFICE
CERTIFICATE OF CORRECTION

PATENT NO. : 5,728,156

DATED : March 17, 1998

INVENTOR(S) : Amitava Gupta et al.

It is certified that error appears in the above-indentified patent and that said Letters Patent is hereby corrected as shown below:

In Claim 4, Col. 12, line 47, after "undergoes" delete "of".

Signed and Sealed this

Second Day of June, 1998

Attest:

BRUCE LEHMAN

Attesting Officer

Commissioner of Patents and Trademarks